(12) United States Patent
Hacker et al.

(10) Patent No.: US 8,857,443 B2
(45) Date of Patent: Oct. 14, 2014

(54) METHOD AND ARRANGEMENT FOR SELECTING AN IOL AND/OR THE SURGICAL PARAMETERS WITHIN THE FRAMEWORK OF THE IOL IMPLANTATION ON THE EYE (75) Inventors: Martin Hacker, Jena (DE); Martin Kuehner, Bad Klosterlausnitz (DE); Rico Fuchs, Jena (DE); Matthias Reich, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 169 days.

(21) Appl. No.: 13/483,938

(22) Filed: May 30, 2012

(65) Prior Publication Data

US 2012/0310337 A1   Dec. 6, 2012

(30) Foreign Application Priority Data

May 31, 2011   (DE) .......................... 10 2011 103 224

(51) Int. Cl.
*A61B 19/00*   (2006.01)
(52) U.S. Cl.
USPC ........................................................... 128/898
(58) Field of Classification Search
CPC ................................ A61B 3/0033; A61B 3/10
USPC ........................................................ 128/898
See application file for complete search history.

(56) References Cited

FOREIGN PATENT DOCUMENTS

WO   WO 02/088830 A1   11/2002

OTHER PUBLICATIONS

Hong, Xin, et al., "Optimizing distance image quality of an aspheric multifocal intraocular lens using a comprehensive statistical design approach," *Optics Express*, vol. 16, No. 25, pp. 20920-20934 (Dec. 2008).

*Primary Examiner* — Howie Matthews
(74) *Attorney, Agent, or Firm* — Patterson Thuente Pedersen, P.A.

(57) ABSTRACT

Selection of an appropriate intraocular lens (IOL) and/or the applicable surgical parameters for optimizing the results of refractive procedures on the eye. Features of the IOL are crucial for the selection and/or adjustment of the optimal IOL, but so is the IOL selection method (and parameters) from a surgical perspective. For the method, corresponding output parameters are determined from predetermined, estimated, or measured input parameters and/or their mean values, wherein at least two input parameters are varied with one another and which have at least one input parameter as a distribution function. The resulting function is optimized by means of corresponding target values and the determined distribution function of one or more output parameters is used as a decision aid. The present solution is used for selecting an appropriate IOL and/or the applicable surgical parameters and is applicable in the field of eye surgery for implanting IOLs.

14 Claims, 6 Drawing Sheets

PRIOR ART

METHOD AND ARRANGEMENT FOR SELECTING AN IOL AND/OR THE SURGICAL PARAMETERS WITHIN THE FRAMEWORK OF THE IOL IMPLANTATION ON THE EYE

CROSS REFERENCE TO RELATED APPLICATIONS

The present application claims priority to and full benefit of German National Patent Application No. DE 10 2011 103 224.3 filed 31 May 2011 the entire contents of which are incorporated herein by reference.

FIELD OF THE INVENTION

This disclosure relates to the field of opthamology and in particular to the appropriate selection and subsequent implantation of an intraocular lens (IOL) in a subject.

BACKGROUND OF THE INVENTION

According to the known prior art, IOLs are selected and/or adjusted on the basis of measured and/or estimated variables, wherein only individual parameters in the form of single measurement values or as a mean value from defined patient groups are taken into account. However, the dependencies from the specific concomitants of the treatment, such as characteristics of the patients, diagnostics, surgical method and the like, as well as the use of statistical distribution for the parameters are not taken into account.

Figure 1:
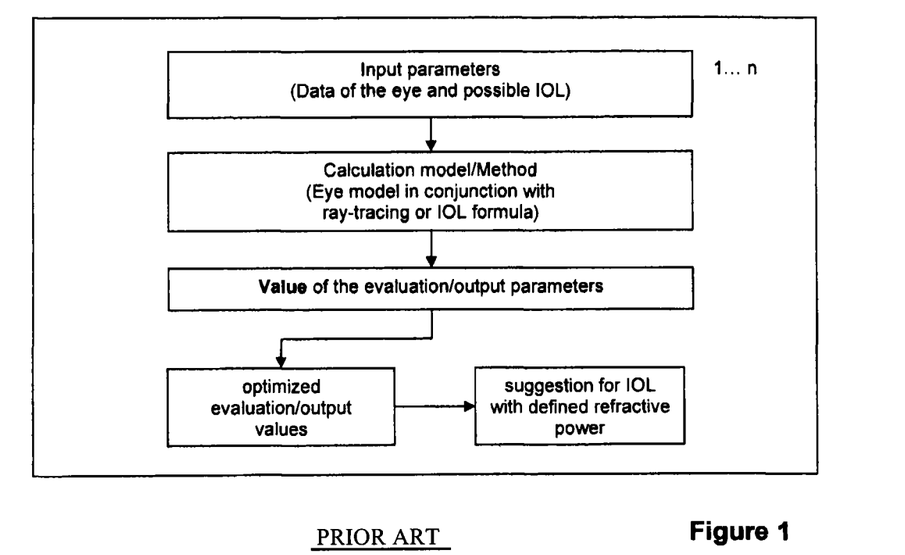
FIG. 1 depicts a sequence for selecting an IOL according to the prior art.

The selection according to the known prior art can be described in accordance with FIG. 1.

The biometric data of the eye to be treated, which are determined using an ophthalmological measuring device as well as the data of the (1 . . . n) IOLs eligible for implantation are the input parameters for the calculation process.

These IOLs typically vary according to IOL type (including variation of their asphericity or toricity) and refractive power of the IOL.

With the use of a calculation model (typically an IOL formula or by means of ray-tracing), an output and/or evaluation parameter (typically, the refraction of the patient after implantation of the IOL) is calculated in the next step. This output and/or evaluation parameter is then optimized through variation of the input parameters selectable by the physician such that the target refraction is obtained.

The currently most prevalent calculation models are so-called IOL formulas, e.g. according to Holladay, Hoffer, Binkhorst, Colenbrander, Shammas, or SRK.

Accordingly, the refraction D (=output/evaluation parameter) of the patient after implantation of the IOL is calculated as $$D = D_{IOL} - f(K, AL, VKT, A) \quad (F1)$$

wherein f( ) is a classically known IOL formula
and $D_{IOL}$ refractive power of the IOL,
K the measured keratometry value,
AL the measured axis length of the eye,
VKT the measured anterior chamber depth, and
A an IOL type-dependent constant, are input values.

For selecting the IOL, the physician predetermines a target refraction (D=$D_{TARGET}$). For the optimization, the physician calculates the refraction according to (F1) for different IOLs through variation of $D_{IOL}$ and A. In many cases, the physician uses IOLs of the same type, so there is no variation in A, and the optimization amounts to a formula calculation according to $D_{IOL} = D_{TARGET} + f(K, AL, VKT, A)$. In case of emmetropia as the target, the classical formula calculation of the IOL is therefore $D_{IOL} = f(K, AL, VKT, A)$.

The constant A in the formulas is determined empirically using a patient group in order to adjust the formula values to the actually resulting optimal refraction values. However, this adjustment merely ensures that the mean value of the refraction values for the test group corresponds with the formula.

Statistical errors of the biometry formula are typically taken into account by the physician such that the physician knows from experience that the actual obtained refraction values for a patient have a certain variation in the target refraction. If the physician wants to minimize their influence, the physician makes a correction to the target refraction. For example, if the physician encounters deviations of +/−0.25D when compared to the target refraction, which is typical for patients with myopic eyes, the physician will aim for a refraction of −0.25D in order to avoid a high probability for the eye of the patient to become intolerably hyperopic. This method is a good strategy for the mean value of the patient group.

However, the typical deviation of the target refraction and/or the margin could be reduced if single input parameters of the individual patient were used as an output variable instead of a mean value from a patient group.

In order to avoid systematic errors, various approaches are currently used according to the prior art.

A number of physicians use a different A-constant for every ethnic group of their patients. This reduces systematic errors and, provided the statistical scattering in the respective group is smaller, also statistical errors.

Depending on defined initial conditions, e.g. patients with long axis lengths or previous refractive cornea surgery, other physicians use different biometry formulas which are better adjusted to the respective conditions or which require the measuring of additional parameters, such as anterior chamber depth or lens thickness. This also reduces particularly the systematic errors, however, statistical errors may increase in part because of the additionally measured parameters.

A somewhat smaller number of physicians use ray-tracing methods, according to P.-R. Preussner and others in Preussner, P.-R. u. a.; "Vergleich zwischen Ray-tracing and IOL-Formeln der 3. Generation" (Comparison between ray-tracing and IOL formulas of the $3^{rd}$ generation), Ophthalmologe 2000, 97:126-141, the contents of which are incorporated herein, as a calculation model instead of simple formulas (FIG. 1). Based on the individual measurement values and estimated variables, particularly the position of the IOL in the eye, an eye model is developed with usually several optically active surfaces and "calculated" according to methods from optics design for one or more rays. The imaging quality on the retina/fovea is calculated as an assessment value. If the input variables are determined with appropriate accuracy, systematic errors can by and large be avoided. However, statistical errors, e.g. due to a lack of reproducibility of the measurements or deviations of the wound healing process, are once again not taken into account.

Some manufacturers of IOLs attempt to compensate for the latter deviations by designing the IOL in such a way that the "active" refractive power of the IOL in the mean, i.e. average eye, is as position-insensitive as possible. Such artificial eye lenses and a method for their improvement are described in WO 2007/128423 A1 the contents of which are hereby incorporated by reference herein. Here, the surface shape of the IOL is modified such that it has a surface shape deviating from the perfect sphere. Thereby, the design of the IOL takes into account the natural optical configuration of the human vision apparatus, e.g. visual axis tilt and pupil decentration. In addition, the design method can account for potential positioning errors caused by implantation and surgery effects. However, deviations in the position of the IOL can ultimately not be taken completely into account or compensated.

According to Warren Hill and Richard Potvin in "Monte Carlo simulation of expected outcomes with the AcrySof toric intraocular lens", BMC Ophthalmology 2008, 8:22, the contents of which are incorporated herein, a Monte Carlo method/simulation can be used for optimizing the selection of toric IOLs with the objective of optimizing the target margin. Similar to the above-mentioned example, the physician is advised, according to Hill and Potvin, to account for a (negative) residual toricity of the "cornea—IOL" system in order to avoid (under-) correction.

In order to arrive at this recommendation, Hill and Potvin calculate the mean postsurgical astigmatism of the "cornea—IOL" system from individual keratometer measurements, from the degree of the IOL selected according to a certain selection strategy, from mean position data of the markings on the eye, from the mean variable of the induced astigmatism, and from the mean postsurgical rotation of the IOL.

This is compared to an actual astigmatism obtained from a simulation. Thereto, the distributions of the induced astigmatism, the marking and the IOL rotation due to measurement uncertainties and deviations in execution and wound healing are used to (purportedly "exactly") simulate a postsurgical astigmatism according to the Monte Carlo method for each of the 2000 patients of the group. The simulated measurement values of the patient group are subsequently averaged separately for every degree of toricity in order to determine the actual/simulated postsurgical astigmatism. According to Hill and Potvin, this procedure is executed for two selection strategies, wherein ultimately the one strategy is selected which has, as a result, a lesser actual/simulated, postsurgical astigmatism averaged from the patient group.

Hill and Potvin thereby show that distributions in patient groups generated with Monte Carlo methods can be used for the selection of the method and optimal IOL (margin). However, Hill and Potvin neither makes reference to the distribution functions generated with the Monte Carlo methods for the individual patient instead of the patient group nor does it constitute an alternative.

Peter N. Lombard and Scott K. McClatchey describe in "Intraocular lens power requirements for humanitarian missions" J. Cataract Refract Surg Vol 25, October 2009, the contents of which are incorporated herein, how the number of types of IOLs to be provided for humanitarian missions can be optimized using the Monte Carlo simulation. Even though priority is given to the number of allocated lens types, the necessity of implementing regional, cultural, gender-specific and age-specific variation for the selection of the IOL types is explicitly apparent.

The solutions known from the prior art are disadvantageous because only individual parameters in the form of single measurement values or as a mean value from defined patient groups, but not their dependency on the individual patients and/or the specific concomitants of the treatment are taken into account for the selection or adjustment of the required IOL and/or the selection of the optimal surgical parameters.

The possible connections between the selected IOL and the surgical method selected for the implantation was examined by T. Iwase and K. Sugiyama in the study "Investigation of the stability of one-piece acrylic intraocular lenses in cataract surgery and in combined vitrectomy surgery", Br J Ophthalmol 2006; 90, 1519-1523, the contents of which are incorporated herein. Therein, a single-piece acrylic IOL was implanted in one eye of the patients and a three-piece acrylic IOL was implanted in the other eye. The recovery was documented through measuring the degree of decentration and incline of the IOL as well as the anterior chamber depth after one (1) week and monthly for up to six (6) months.

From the result, it was ascertained that there were no distinctive changes regarding mean decentration and incline but a measurement of the anterior chamber depth showed significant differences. While the anterior chamber depth did not change after implanting the single-piece IOL, a significant flattening of the anterior chamber occurred in the eyes with an implanted three-piece IOL.

SUMMARY OF THE INVENTION

The present disclosure teaches appropriate selection of an IOL and/or the applicable surgical parameters for optimizing the results of refractive procedures on the eye. While the features of the IOL are crucial for the selection and/or adjustment of an optimal IOL, the method to be selected and/or its parameters are taken into account for the surgical parameters.

For the method, according to the disclosure hereof, corresponding output parameters are determined from predetermined, estimated, or measured input parameters and/or their mean values, wherein at least two input parameters are varied with one another and which have at least one input parameter as a distribution function. The resulting distribution function(s) is/are optimized by means of corresponding target values and the determined distribution function(s) of one or more output parameters is/are used as the decision aid.

The present solution is used for selecting an appropriate IOL and/or the applicable surgical parameters and is applicable in the field of eye surgery for implanting intraocular lenses.

The present disclosure addresses the problem of providing a method and an arrangement for the optimized selection of an IOL and/or the surgical parameters within the framework of the IOL implantation. Proceeding from single input parameters in the form of statistical distributions and corresponding target values, the user is to be provided with output parameters as objective decision aids which significantly simplify and specify the selection(s).

For the method for selecting an IOL and/or the surgical parameters within the framework of the IOL implantation, according to the disclosure, corresponding output parameters are determined from predetermined, estimated, or measured input parameters and/or their mean values, wherein at least two input parameter are varied with one another and which have at least one input parameter as a distribution function and the resulting distribution function(s) is/are optimized by means of corresponding target values and the determined distribution function(s) of one or more output parameters is/are used as the decision aid.

Hereby, two input parameters are varied with one another by determining possible combinations for the two (variable) input parameters and incorporating them in a model. Thereby, at least one input parameter is a distribution function.

The arrangement, according to the disclosure, comprises an input unit, a central control and evaluation unit and an output unit. An interface to a data source is provided as an input unit. An available graphical user interface is used for selecting input parameters from an available database, wherein at least one input parameter is a distribution function.

The central control and evaluation unit is capable of varying at least one input parameter in the model by means of a calculation model, optimizing the resulting distribution function(s) by means of corresponding target values and determining at least one distribution function of one or more output parameters as a decision aid and render and/or depict at least one distribution function of one or more output parameters as a decision aid using the graphical user interface designed for this purpose.

The purpose of the present disclosure is the selection of an appropriate IOL to and/or the applicable surgical parameters. The disclosure is applicable in the field of eye surgery for implanting IOLs. For the selection and/or adjustment of the optimal IOL, the surgical parameters, particularly the method to be selected and/or its parameters, e.g. incision size, incision angle, and incision depth are taken into account in addition to its features, e.g. type, refractive power, asphericity, multifocality and the like.

DETAILED DESCRIPTION OF THE INVENTION

For the method of selecting an IOL and/or the surgical parameters within the framework of an IOL implantation, according to the disclosure, corresponding output parameter are determined from predetermined, estimated, or patient-specific measured input parameters and/or their mean values, wherein at least two input parameter are varied with one another and which have at least one input parameter as a distribution function and the resulting distribution function(s) are optimized by means of corresponding target values and the at least one determined distribution function of one or more output parameters is used as a decision aid. Thereby, the input parameters can contain data related to that of the eye, the patient, the IOL, the diagnostic or measuring device, and surgical parameters.

According to a first advantageous embodiment of the method, the biometric parameters, such as axis length, anterior chamber depth, and corneal radii of the eye of a patient to be treated are measured. Preferably, an IOLMaster® from Carl Zeiss Meditec AG of Jena, Germany is used for this purpose, with which the required data of the human eye can be determined consecutively in one sitting. The biometric measuring device excels in its excellent patient comfort because all measurements are taken with the non-contact method.

The biometric data of the eye to be treated thus determined are used as input parameters. Together with additional input parameters, e.g. patient data and data from the IOL, the diagnostic or measuring device as well as surgical parameters, the values of the input parameters are varied with one another using a calculation model. The patient data or surgical parameters, e.g. can additionally be ascertained beforehand in clinical studies.

The following parameters can be used as input parameters, wherein at least one input parameter is a distribution function:
- Measured biometric data: Cornea shape, thickness, and position; axis length; lens shape, thickness, and position; anterior chamber depth, retina thickness, chamber angle, etc. Thereby, the measurement values may be available with the fluctuation margins/distribution known from the measuring device, wherein the fluctuation margins can be measured or calibrated specifically for each measuring device or originate from statistical analyses of clinical tests.
- IOL parameter: Such as IOL model, haptic setup, thickness, and curvatures (form parameters), solidities and elasticities (mechanical parameters), refractive indices (material parameters), refractive power, etc. The probability distributions for the postsurgical position or other postsurgical results of specific IOL models, haptic geometries or the like can hereby be statistically determined, e.g. through clinical tests.
- Unmeasured or not measurable values, such as refractive index of the vitreous humor, cornea thickness, anterior chamber depth, accommodative capacity or lens movement, from estimations based on patient parameters, such as ethnicity, age, gender, pathological history, etc. Unmeasured but known values, e.g. from literature, have often been determined with value and probability distribution. Clinical results are statistically determined and published particularly for group-specific values, such as ethnicity, age, gender, etc. and can therefore be used as input distributions.
- Surgical parameters: Type, procedure, technique, etc. and their effects on the location and position of the IOL during healing. Parameters generated by postsurgical results, e.g. the cylinder induced by the various incision options may also be available from clinical tests with probability distribution.
- Parameters of the diagnostic device: Type, procedure, measuring errors, etc. Measuring parameters with specified probability distribution or measurement accuracy can also be determined with a measuring device. However, this is only an exemplary list because, in principle, other input parameters known to a person skilled in the art can also be used.

According to the disclosure, all input parameters for an eye model are calculated in the calculation model using ray-tracing or biometric calculation formulas and individual frequency distributions of the output parameters are determined through a Monte Carlo simulation. Hereto, the known biometry formulas, e.g. according to Holladay, Hoffer, Binkhorst, Colenbrander, Shammas, or SRK, can be used.

According to a second advantageous embodiment of the method, the individual frequency distributions of the output parameters can be determined with an error distribution optimization instead of a Monte Carlo simulation. In this case, error distribution optimization signifies the best possible adjustment of an actual-target distribution to a nominal-target distribution, i.e. minimization of the deviation of the target distribution from a nominal-target distribution. This can be achieved with any known iterative parameter variation.

In conventional Gauss distributions, the error of the result value can easily be determined using error propagation calculation with mean value and standard deviation. Once at least one of the input distributions is not Gaussian shaped, the error propagation calculation can no longer be applied.

For such cases, the variation using simulation is particularly advantageous. For such simulations for selecting the input parameters for a predetermined output distribution, iterative approximation and/or regression methods are used. In addition to a Monte Carlo simulation, simulations according to Levenberg, Marquart, Gauss-Newton or the like can be used, depending on the complexity of the varied parameters.

For determining the individual frequency distribution using error distribution optimization, the local (by the applicable measured, estimated, adjusted value) partial derivative, according to the input parameters, is formed with the help of the appropriate calculation rule of the output parameter. Said derivative is then multiplied by the standard deviation of the appropriate input parameter.

Subsequently, the individual standard deviation for the output parameter is calculated according to known methods (such as the root of the sum of the squares of the foregoing product). Then the individual frequency distribution of the output parameter is determined from the determined individual output value and the individual standard deviation.

The variation of one or more input parameters for minimizing the deviation from mean value and distribution function with regard to one or more freely selectable target values is achieved both with the Monte Carlo simulation and the error distribution optimization.

Based on these individual frequency distributions, the operator can then adjust an individual risk margin with regard to the refraction to be achieved. Thereto, risk and/or benefit profiles are used as target values.

While the risk profiles which are used as target values originate primarily from patient data and surgical parameters, the benefit profiles, which are used as target values, are primarily based on the evaluation of the eye after the refractive procedure, particularly with regard to imaging quality, contrast, resolution, aberration, focus depth, quality of the imaging scale, and refraction.

With the method, according to the disclosure, the distribution function(s) of the output parameter(s) which is(are) used as decision aid is(are) determined in accordance with the target values and rendered or displayed to the operator for decision making.

Depending on the problem, the following output parameters can be taken into consideration:
  Evaluation of the image of the retina with regard to moments, entropy, compactness, shape, or intensity distribution using the point spread function (PSF), line spread function (LSF) or root mean square,
  Evaluation of the resolution using optical transfer function (OTF), such as modulation transfer function (MTF) or phase transfer function (PTF),
  Evaluation of the contrast using the contrast sensitivity function (CSF),
  Evaluation of the optical aberrations, such as chromatic aberration, beam aberration, wave front aberration, focus depth, and binocular deviation of the imaging scale,
  Evaluation of the classic refraction parameters diopter and astigmatism.

Once again, this is only an exemplary list because, in principle, other optical evaluation parameters known to a person skilled in the art can also be used.

According to a further advantageous embodiment of the method, only those distribution functions of the output parameters are rendered or displayed for the operator's decision making which best correspond to the predefined target values.

Furthermore, it is possible to render or display as a matrix the two or more distribution functions of the output parameters, which are used as the decision aid.

In a last method step, the operator selects an IOL and/or surgical parameters on the basis of the rendered or displayed distribution functions of the output parameters.

However, if the operator is unable to select an IOL and/or surgical parameters, the operator can define new target values and start the method, according to the disclosure, from the beginning.

Of course, this also applies if a sufficient optimization of the target function is unsuccessful or the operator is dissatisfied with the rendered or displayed distribution functions of the output parameters.

Figure 2:
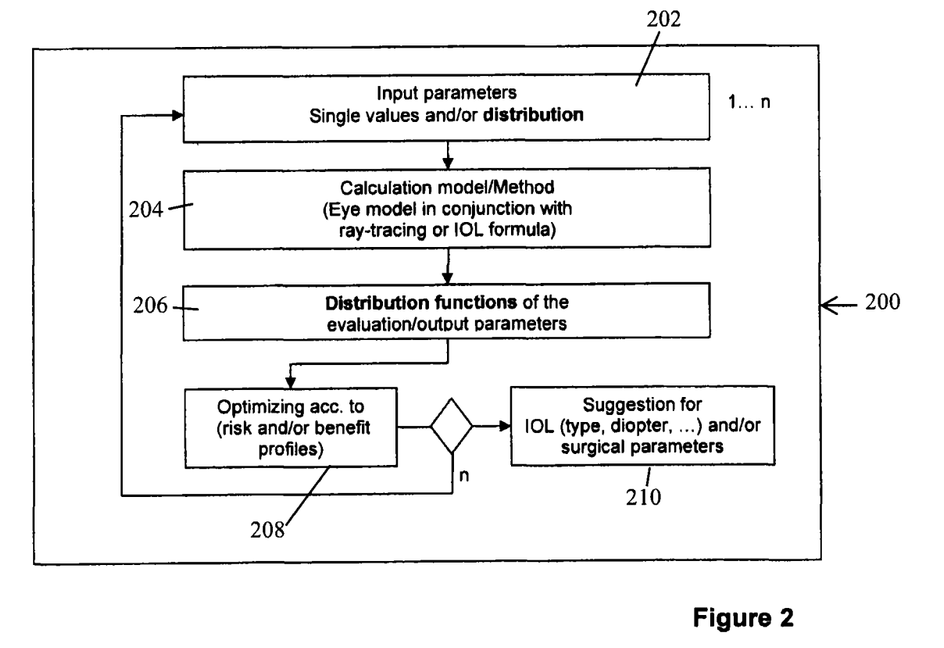
FIG. 2 depicts a general sequence for selecting an IOL and/or surgical parameters according to the method of the instant disclosure.

Thereto, FIG. 2 shows the sequence for selecting an IOL and/or surgical parameters according to the method of the disclosure.

In contrast to the method according to the prior art as described in FIG. 1, not only the biometric data of the eye to be treated, which were determined with an ophthalmological measuring device, and the data of the applicable IOLs in the form of single values are used as input parameters. Instead, data of the patient, the diagnostic or measuring device, and surgical parameters in the form of distribution functions can be introduced (at 202) into the method (200).

The n input parameters are also varied with one another and included in a calculation model, e.g. an eye model, using ray-tracing or biometry formulas (204). The values for the evaluation parameters resulting from the calculation are, in accordance with the input parameters, also available as distribution functions of the evaluation parameters (206), are optimized using selected risk and/or benefit profiles (208) and presented to the operator for decision making (210).

The operator can select an IOL and/or surgical parameters using the rendered or displayed distribution functions of the output parameters. In contrast to known methods, the operator can select the IOL not only in accordance with its refractive power value but also on the basis of manufacturer, type, material, etc., for example. In addition, the surgical parameters which are optimal for the procedure can also be selected.

However, if the operator is unable to select an IOL and/or surgical parameters, or the optimization does not appear optimal, the operator can define new target values and re-start the method 200, according to the disclosure, from the beginning.

According to a last advantageous embodiment of the method, those input parameters can be marked which have the best chances for improving the results and, e.g. a new measurement with another measuring device is automatically suggested to the operator.

Figure 3:
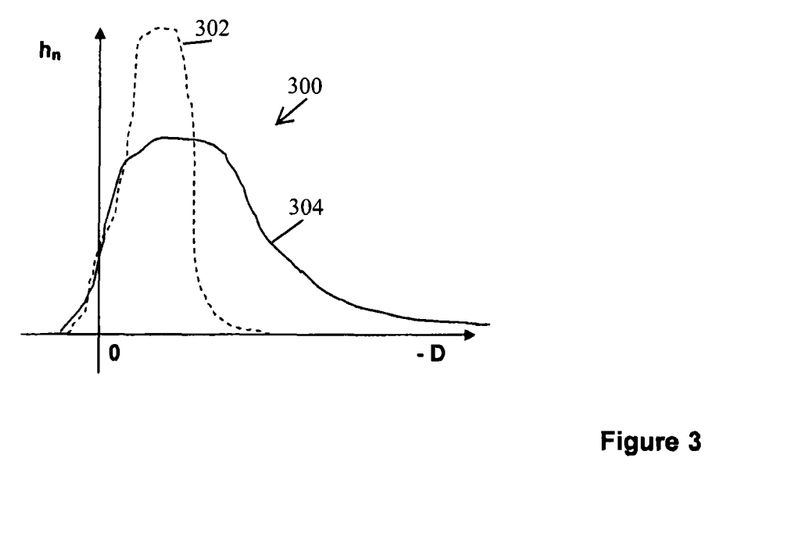
FIG. 3 depicts in graphical form the output from two distribution functions, optimized with regard to the target refraction, provided to the user for decision making.

FIG. 3 shows exemplary distribution functions rendered for the operator's decision making. FIG. 3 depicts in graphical form 300 the output from two distribution functions, optimized with regard to the target refraction, provided to the user for decision making. In addition to the data of available IOLs, the biometric data of the eye to be treated, which were determined with different ophthalmological measuring devices, can be used as input parameters. The graph 300 of FIG. 3 only shows two distributions 302, 304 (most consistent with the target values) of the relative frequency $h_n$ as a function of the target refraction D.

For the distribution function for a spherical IOL 302 (depicted as a dotted line), the biometric data of the eye to be treated were determined, e.g. with a keratometer. By contrast, the other distribution function 304 (depicted as a solid line)

was determined for a multifocal IOL and the biometric data were measured with a topography device.

On the basis of these distribution functions, the physician would be able to tell the myopic patient and himself/herself that the patient would become emmotrope based on a spherical IOL in conjunction with reproducible keratometer values, while the multifocal IOL would result in a certain presbyopia correction, due to the multifocality, with a more uncertain mean refraction D.

The selection of the IOL type by physician or patient depends on whether a correaction for a specific imaging distance or for a greater range is desired.

While the IOL type with the dotted line 302 in FIG. 3 is more suitable for correcting a specific imaging distance due to its narrow distributions of the relative frequency $h_n$, the IOL type depicted as solid line 304 in FIG. 3 is better suited for a correction over a greater range (presbyopia) because the position of the mean diopter D would be less certain than for the IOL type with the dotted line 302.

Figure 4:
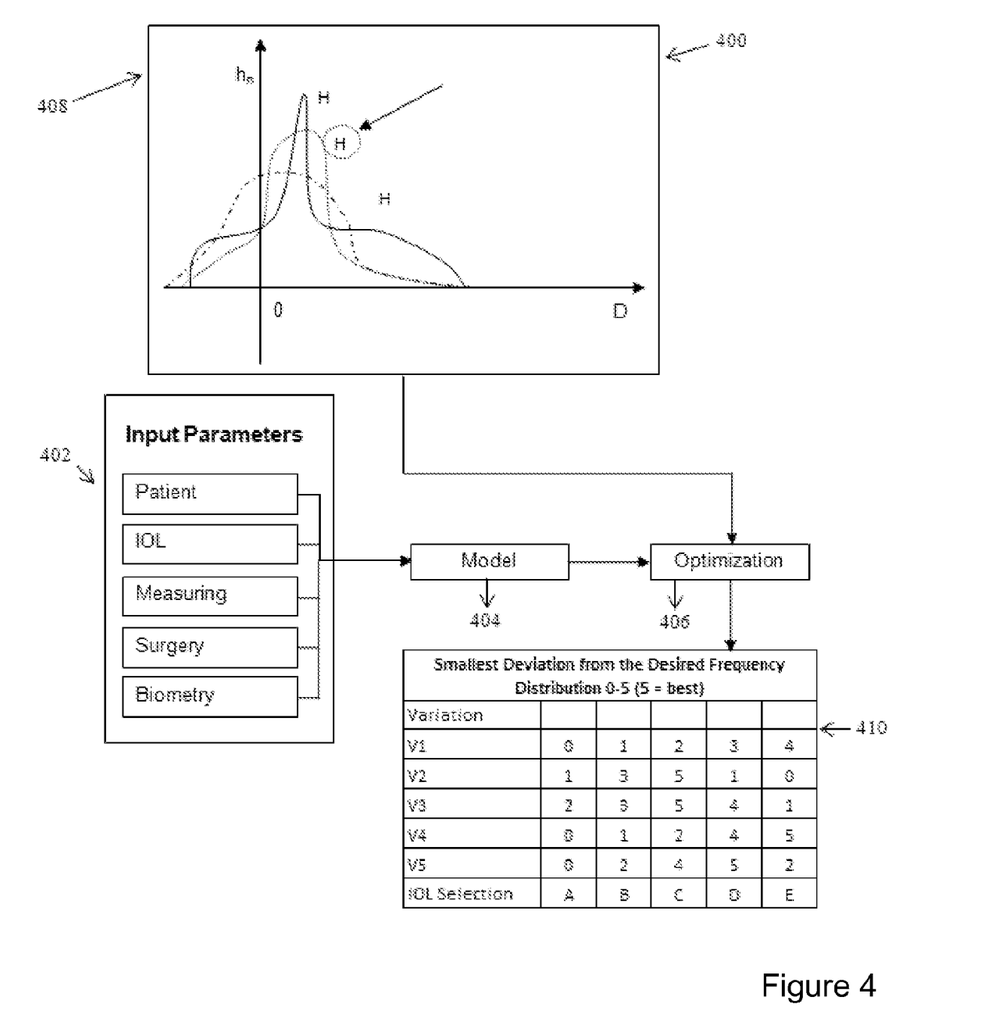
FIG. 4 illustrates a detailed sequence for selecting an IOL and/or surgical parameters according to the method of the disclosure.

In the following, the method, according to the disclosure, is described on the basis of the detailed sequence 400 for selecting an IOL and the surgical parameters as shown in FIG. 4. In the first part for determining the input parameters 402, the biometric parameters (axis length, anterior chamber depth, and corneal radii) of the patient's eye to be treated are measured. Preferably, an IOLMaster® from Carl Zeiss Meditec AG of Jena, Germany is used for this purpose, which determines the required data consecutively in one sitting with the non-contact method.

On the basis of the biometric data and additionally ascertained patient data, such as age, ethnicity, gender, refractive error or the like, an eye model is then formed (at 404), wherein the input parameters are incorporated not only in the form of single values but also as statistical distributions. These, e.g. were determined beforehand in clinical studies.

From a database, IOLs are selected consecutively which are also based on model parameters in the form of distribution functions which, e.g. are based on manufacturing tolerances with regard to thickness, curvatures, refractive index or the like. These distribution functions are also incorporated mathematically into the eye model (at 404).

All input parameters (from 402), at least one of which is a distribution function, are varied with one another by calculating them into the eye model 404 using ray-tracing or biometric calculation formulas and individual frequency distributions of the output parameters are determined, e.g. through a Monte Carlo simulation.

The upper section of FIG. 4 shows the determined frequency distributions of the output parameters 408 from which the operator selects an appropriate target value. In the depicted example, distribution H2 (circled in ghost with an arrow) comes closest to the operator's opinion and is selected for optimizing the distribution functions (at 406).

For the subsequent optimization, 5 possible IOLs (A, B, C, D, and E) with also 5 applicable surgery variations (V1, V2, V3, V4, and V5) are varied. This results in a matrix (410) which shows the deviations of the individual combinations from the desired frequency distribution. Thereby, the matrix 410 can contain all possible variations or an already limited selection. Although not shown as such in FIG. 4, the depiction is preferably in color which simplifies the selection for an operator.

By simple inspection and with reference to the deviation scores of five (5) therein, the combinations V2-C, V3-C, V4-E, and V5-D depicted in the matrix 410 in the lower section of FIG. 4 show the smallest deviations from the target distribution H2 selected by the operator. Therefore, the selection should be focused on those four (4) variations. The operator can base the selection on personal preferences with regard to to the surgical technique or with regard to the availability of a given IOL.

Figure 5:
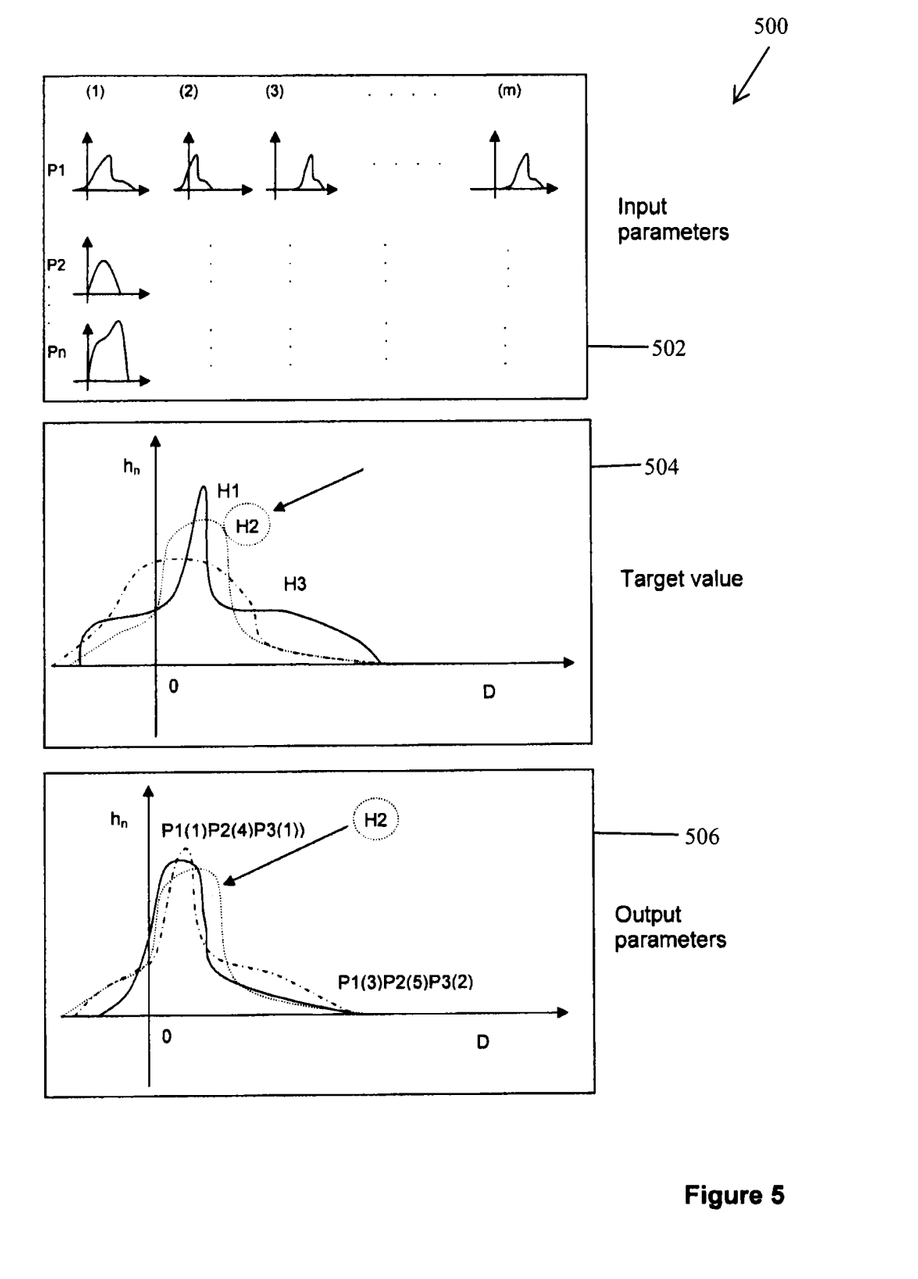
FIG. 5 illustrates in three distinct frames possible input parameters, target values, and optimized output parameters, respectively, for selecting an appropriate IOL for a subject.

FIG. 5 shows a juxtaposition in three frames 500 of possible input parameters 502 of the target values 504 to be selected and the output parameters 506 optimized for the selection. The upper frame 502 in FIG. 5 shows the distribution functions for the input parameters P1 to Pn. Thereby, there are m possible variations per input parameter. Thus a dot product of the "n" and "m" values (i.e., n·m) which represent input/distribution functions can, as shown in the graph 502, preferably be depicted in a matrix.

The second frame 504 in FIG. 5 shows examples of relative frequency distributions (H1, H2, H3, in solid, dotted, and dashed line representations, respectively) from which a target value 504 can be selected. For reasons of simplification, only three (3) frequency distributions are depicted, wherein H1 is the progressive, H2 the optimistic, and H3 the conservative variation, as an interpretation. As a target value, the operator selects the distribution which to his/her knowledge appears to have the best chances for success for the present case. In the present case, e.g. H2 is defined as the target value (depicted with an arrow directed toward "H2" which is circled by a dotted line).

With the use of the eye model, it is calculated in the following, which of the combinations of input parameters best corresponds to the selected target distribution.

Thereto, the lower frame 506 in FIG. 5 shows the frequency distributions of combinations [P1(1), P2(4), P3(1)] and [P1(3), P2(5), P3(2)] which most closely correspond to the target value (H2). For reasons of clarity, target value H2 is also depicted in the third frame 506 of FIG. 5.

The combinations [P1(1), P2(4), P3(1)] and [P1(3), P2(5), P3(2)] best correspond to the target value H2 selected by the operator and are recommended as the combination of the IOL to be implanted with the appropriately applicable surgical parameters.

Figure 6:
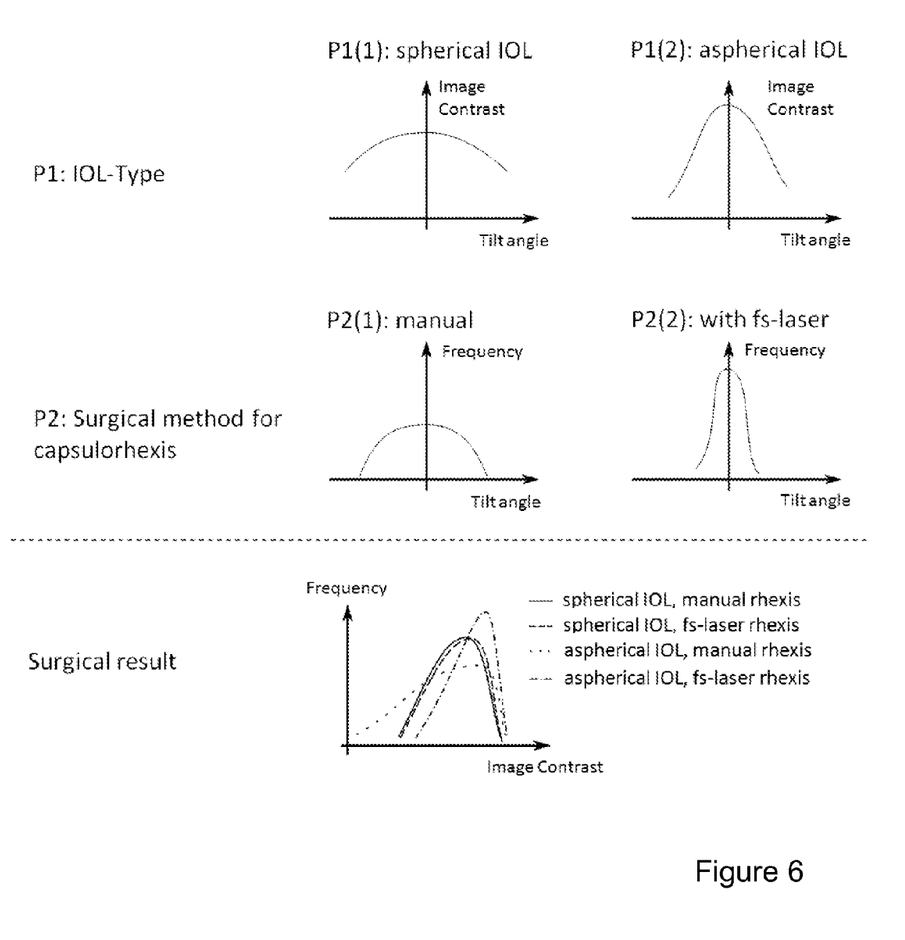
FIG. 6 provides an exemplary depiction of the distribution functions for 2 different IOL types and surgical methods for each.

FIG. 6 shows a concrete example 600 for the combination of different distribution functions including German-English translated terms appears below the example 600. Two different IOL types (spherical IOL and aspherical IOL, respectively, at 602) and two different surgical techniques (manual and using a femtosecond (fs) laser, respectively, at 604) are randomly chosen as input parameters.

Spherical and aspherical IOLs are considered as IOL types at 602. As is known spherical IOL cannot compensate the spherical aberrations of the eye, and therefore, the maximum attainable image contrast on the retina is slightly reduced. However, the result is largely independent from the tilt angle of the IOL in the eye. By contrast, high image contrast can be obtained with an aspherical IOL and ideal positioning; however, the disadvantage is a low tolerance with regard to tilting.

For the surgical methods, two methods for capsulorhexis are shown at 604. The manual method often leads to deviations from the ideal form, which is circular and centered; however, with the new cataract devices which are based on femtosecond (fs) lasers, the incision can be made automatically and therefore with much greater accuracy. Therefore, the resulting tilt angle of the IOL relative to the optical axis in the eye can be expected to be significantly reduced with the new method. Quantitatively, the distribution functions for the input parameter variations shown in the upper section of FIG. 6 are a result of the described dependencies.

When these distribution functions are varied with one another, according to the6disclosure, the result as shown in the lower section of FIG. 6 in the form of the four (4) distribution functions for the output parameter "image contrast" is obtained. Upon inspection of this portion of FIG. 6 it is apparent that the technically elaborate cataract surgery with an fs laser results in significant advantages only for the aspherical IOL. Therefore, depending on the patient's willingness to pay, the physician should select the combination "spherical IOL with manual technique" or the relatively "premium" combination "aspherical IOL with fs technology."

Figure 7:
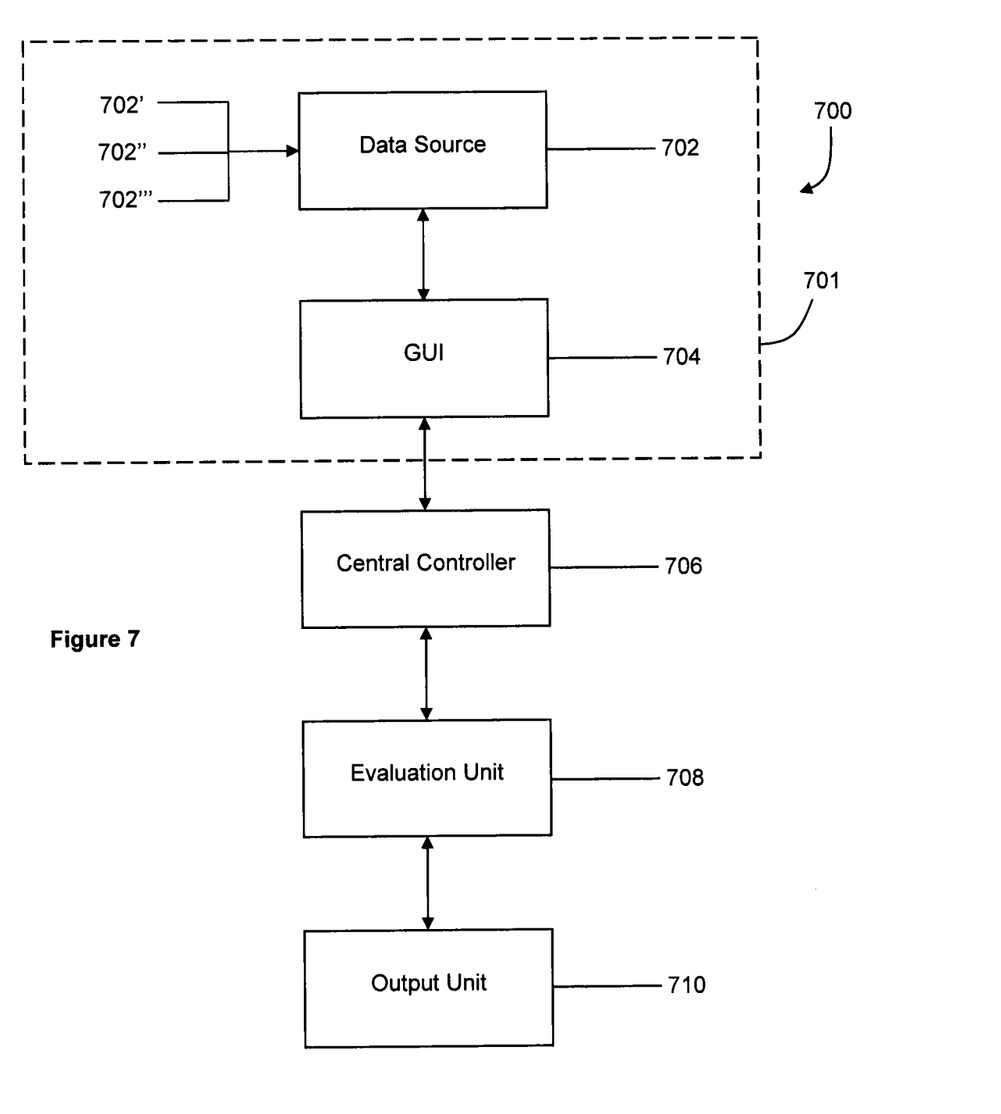
FIG. 7 is a block diagram of an arrangement for selecting an IOL and/or the surgical parameters for procedures on the eye within the framework of an IOL implantation according to an embodiment of the invention.

Thus in summary the arrangement for selecting an IOL and/or the surgical parameters for procedures on the eye within the framework of an IOL implantation, according to the disclosure, comprises an input unit 701,702,702',702", 702''' (for receiving the input parameters, per the step 202 of the method 200 depicted in FIG. 2), a central control 706 (per steps 204, 206) and evaluation unit 708 (per step 208)—which can be combined into a single unit—and an output unit 710 (per step 210).

An interface to a data source is provided as the input unit 701-702, wherein one or more ophthalmological measuring devices, such as biometry or topography measuring devices, wavefront measuring devices, measuring devices for optical coherence tomography (OCT), or slit light measuring devices serve as the data source 702. It is particularly advantageous when the ophthalmological measuring devices which serve as data sources are integrated in a network (illustrated by 702', 702",702''' and connected to the arrangement 702, according to the disclosure.

It is particularly preferred that, in addition to the measurement data, calibration data of the measuring device and the distribution of the measurement accuracy of the ophthalmological measuring device are also transmitted or made available.

Furthermore, the arrangement, according to the disclosure, comprises a graphical user interface 704 for selecting input parameters from an available database, wherein at least one input parameter is a distribution function.

Thereby, the database can be accessed locally, via network or online. In case of a public database, providing continuously updated, statistical data from a network is desirable, wherein the data of all measuring devices incorporated in the network are amalgamated. The available database could contain the following input parameters, wherein the list is merely exemplary because, in principle, other input parameters known to a person skilled in the art can also be used:

Measured biometric data: Cornea shape, thickness, and position; axis length; lens shape, thickness, and position; anterior chamber depth, retina thickness, chamber angle, etc. Hereby, the measurement values may be available with the fluctuation margins/distribution known from the measuring device, wherein the fluctuation margins can be measured or calibrated specifically for each measuring device or originate from statistical analyses of clinical tests.

IOL parameter: such as IOL model, haptic setup, thickness, and curvatures (form parameters), solidities and elasticities (mechanical parameters), refractive indices (material parameters), refractive power, etc. The probability distributions for the postsurgical position or other postsurgical results of specific IOL models, haptic geometries or the like can hereby be statistically determined, e.g. through clinical tests.

Unmeasured or not measurable values, such as refractive index of the vitreous humor, cornea thickness, anterior chamber depth, accommodative capacity or lens movement, from estimations based on patient parameters, such as ethnicity, age, gender, pathological history, etc. Unmeasured but known values, e.g. from literature, have often been determined with value and probability distribution. Clinical results are statistically determined and published particularly for group-specific values, such as ethnicity, age, gender, etc. and can therefore be used as input distributions.

Surgical parameters: Type, procedure, technique, etc. and their effects on the location and position of the IOL during healing. Parameters generated by postsurgical results, e.g. the cylinder induced by the various incision options may also be available from clinical tests with probability distribution.

Parameters of the diagnostic device: Type, procedure, measuring errors, etc.

Measuring parameters with specified probability distribution or measurement accuracy can also be determined with a measuring device. Furthermore, the central control unit 706 and evaluation unit 708 are capable of varying at least two input parameters with one another by means of a calculation model, optimizing the resulting distribution function(s) by means of corresponding target values and determining at least one distribution function of one or more output parameters as a decision aid for an operator. As noted previously, the available database can advantageously be incorporated in a network and connected with the arrangement, according to the disclosure.

The central control unit 706 and the evaluation unit 708 are capable of including mathematically all selected input parameters in an eye model using ray-tracing or biometric calculation formulas and determining individual frequency distributions of the output parameters using a Monte Carlo simulation. Also, the known biometry formulas, e.g., according to Holladay, Hoffer, Binkhorst, Colenbrander, Shammas, or SRK, can be used.

In this context, determining the individual frequency distribution of the output parameters is significantly simplified if the distribution functions of the input parameters are substantially Gaussian distributions. In this case, a simplified error distribution optimization instead of a Monte Carlo simulation can be performed.

For determining the individual frequency distribution using error distribution optimization, the local (by the applicable measured, estimated, adjusted value, etc.) partial derivative according to the input parameters is formed with the help of the appropriate calculation rule of the output parameter. Said derivative is then multiplied by the standard deviation of the appropriate input parameter.

Subsequently, the individual standard deviation for the output parameter is calculated according to known methods (such as the root of the sum of the squares of the foregoing product). Then the individual frequency distribution of the output parameter is determined from the determined individual output value and the individual standard deviation. Thus, the central control and evaluation unit 706,708 is capable of determining the variation of one or more input parameters for minimizing the deviation from mean value and distribution function with regard to one or more freely selectable target values with both the Monte Carlo simulation and the error distribution optimization.

According to the disclosure, the available graphical user interface 704 is designed such that the freely selectable target values are entered or selected and the at least one determined distribution function of one or more output parameters is rendered or displayed as a decision aid for an operator.

Risk and/or benefit profiles can be used as target values. While the risk profiles which are used as target values originate primarily from patient data and surgical parameters, the benefit profiles which are used as target values are primarily based on the evaluation of the eye after the refractive procedure, particularly with regard to imaging quality, contrast, resolution, aberration, focus depth, quality of the imaging scale, and refraction.

The central control and evaluation unit 706,708 determines the distribution function(s) of the output parameter(s) which is/are used as a decision aid in accordance with the target values and renders or displays them for decision making using the graphical user interface 704. It is possible for the graphical user interface 704 to also render or display as a matrix the two or more distribution functions of the output parameters, which are used as the decision aid.

Depending on the problem, the following output parameters can be taken into consideration:
- Evaluation of the image of the retina with regard to moments, entropy, compactness, shape, or intensity distribution using the point spread function (PSF), line spread function (LSF) or root mean square,
- Evaluation of the resolution using optical transfer function (OTF), such as modulation transfer function (MTF) or phase transfer function (PTF),
- Evaluation of the contrast using the contrast sensitivity function (CSF),
- Evaluation of the optical aberrations, such as chromatic aberration, beam aberration, wave front aberration, focus depth, and binocular deviation of the imaging scale,
- Evaluation of the classic refraction parameters diopter and astigmatism.

Once again, this is only an exemplary list because, in principle, other optical evaluation parameters known to a person skilled in the art can also be used.

It is particularly advantageous when the ophthalmological measuring devices which serve as data sources 702',702", 702''' and the available database are integrated in a network (with additional network interfaces) and connected to the central control and evaluation unit 706,708.

In an advantageous embodiment, the available graphical user interface 704 is capable of rendering or displaying as a decision aid only those distribution functions of one or more output parameters which best correspond to the freely selectable target values. Thus according to the present disclosure a solution for selecting an appropriate IOL and/or the applicable surgical parameters for optimizing the selection is provided.

Proceeding from single input parameters in the form of statistical distributions and corresponding target values, the user is provided with output parameters as objective decision aids which significantly simplify the selection and increase the chances for success.

To reprise some portions of the foregoing description, for selecting and/or adjusting the optimal IOL, the surgical parameters, particularly the method to be selected and its parameters, e.g. incision size, incision angle, and incision depth, are taken into account in addition to the features of the IOL, such as type, diopter, asphericity, and multifocality. A significant difference with regard to the known method (illustrated in FIG. 1 using averaged margin and/or output parameter from a population) may appear small. This is certainly true for an "average" patient or when the calculations are linear with regard to the input parameters. However, the more a patient deviates from the average patient and the more non-linear the calculation (e.g. with ray-tracing), the greater the impact of the remaining variations of the input parameters.

The arrangements and/or methods, according to the disclosure, are particularly beneficial for IOLs which differ from the standard design in the form of simple spherical surfaces. Multifocal or accommodating IOLs, e.g. can only be characterized by a single refractive power with very rough approximation.

Therefore, a calculation and characterization of the expected surgical outcome using distribution functions is clearly more accurate.

In addition to the application area of cataract surgery, the claims of the described methods and arrangement, according to the disclosure, also comprise similar procedures on the eye known to a person skilled in the art. Those include particularly refractive procedures, such as implantation of intracorneal rings or corneal incisions to compensate for astigmatism. Thereby, the latter procedures, also called "limbal relaxing incisions," can be made with a scalpel or a laser.

The invention claimed is:

1. A computer implemented method for selecting an intraocular lens (IOL) and/or the surgical parameters in the context of IOL implantation procedure for a subject, comprising:
    receiving input at a central control and evaluation unit via an interface from one or more data source ophthalmological measuring devices that are operably coupled to the central control and evaluation unit;
    varying at least two input parameters selected from a list consisting of: a measured biometric data parameter, an IOL-specific parameter, a surgical procedure parameter, a post-surgical result parameter, and a diagnostic device parameter from the one or more data source ophthalmological measuring devices by application of the central control and evaluation unit; and
    providing a decision aid output signal from the central control and evaluation unit related to an optimized IOL for a given patient based on a corresponding output parameter, wherein the optimized IOL is generated via a distribution function based on at least one of said at least two input parameters and optimized by application of a predefined target function,
    wherein the corresponding output parameter is determined from at least one of the at least two input parameters, said input parameters configured as one of: a predetermined value input parameter, an estimated value input parameter, and a measured value input parameter, or a mean value thereof.

2. A method according to claim 1, wherein the input parameters comprise data related to one of: an eye planned for IOL implantation and the IOL implantation subject.

3. A method according to claim 1, wherein the measured biometric data relates to the eye planned for IOL implantation.

4. A method according to claim 1, further comprising using a calculation model to vary the values of the input parameters.

5. A method according claim 1, further comprising applying one of a ray-tracing technique and a biometric calculation formula, and
    wherein individual frequency distributions of the output parameters are determined through one of: an iterative approximation and a regression method.

6. A method according to claim 1, further comprising applying one of a ray-tracing technique and a biometric calculation formula, and
    wherein the individual frequency distributions of the output parameters is determined via an error distribution optimization.

7. A method according to claim 6, wherein the individual frequency distributions signify the variation of one or more input parameters for minimizing the deviation from a mean value and the distribution function with regard to one or more freely selectable target values.

8. A method according to claim 1, wherein one of a risk profile and a benefit profile is used as a target value.

9. A method according to claim 1, wherein a risk profile is used as a target value and is based primarily on at least one of: the measured biometric data parameter and the surgical procedure parameter.

10. A method according to claim 8, wherein the benefit profile is based primarily on a post-surgical evaluation of the eye, at least in regard to: an imaging quality metric, a contrast metric, a resolution metric, an aberration metric, a focus depth metric, a quality of the imaging scale metric, and a refraction metric.

11. A method according to claim 1, further comprising displaying the decision aid output signal so the operator can view same for decision making.

12. A method according to claim 11, further comprising displaying only those distribution functions of the output parameters which best correspond to the predefined target values.

13. A method according to claim 11, further comprising displaying as a matrix at least two distribution functions of the output parameters that are used to render the decision aid output signal.

14. A method according to claim 12, further comprising presenting to an operator at least one of: a specific IOL device and a surgical parameter based on the displayed distribution functions.

\* \* \* \* \*

UNITED STATES PATENT AND TRADEMARK OFFICE
CERTIFICATE OF CORRECTION

| | | |
|---|---|---|
| PATENT NO. | : 8,857,443 B2 | Page 1 of 1 |
| APPLICATION NO. | : 13/483938 | |
| DATED | : October 14, 2014 | |
| INVENTOR(S) | : Martin Hacker et al. | |

It is certified that error appears in the above-identified patent and that said Letters Patent is hereby corrected as shown below:

IN THE SPECIFICATION

Col. 9, line 11, delete "correaction" and insert --correction--

Col. 10, line 66, delete "the6disclosure" and insert --the disclosure--

Signed and Sealed this
First Day of December, 2015

Michelle K. Lee
*Director of the United States Patent and Trademark Office*